United States Patent [19]
Fuchs et al.

[11] Patent Number: 6,136,527
[45] Date of Patent: Oct. 24, 2000

[54] POLYPEPTIDES DERIVED FROM PROTEINS OF THE HEPATITIS C VIRUS, TEST KITS CONTAINING THESE POLYPEPTIDES AND VACCINES AGAINST INFECTIONS OF HEPATITIS C VIRUSES

[75] Inventors: Klaus Fuchs, Deisenhofen; Manfred Motz, München; Michael Roggendorf, Essen; Erwin Soutschek, Berg, all of Germany

[73] Assignee: Roche Diagnostics GmbH, Mannheim, Germany

[21] Appl. No.: 08/078,271

[22] PCT Filed: Dec. 20, 1991

[86] PCT No.: PCT/DE91/01020

§ 371 Date: Oct. 15, 1993

§ 102(e) Date: Oct. 15, 1993

[87] PCT Pub. No.: WO92/11370

PCT Pub. Date: Jul. 9, 1992

[30] Foreign Application Priority Data

Dec. 21, 1990 [DE] Germany ............... 40 41 304

[51] Int. Cl.[7] .................................. G01N 33/576
[52] U.S. Cl. .............. 435/5; 436/518; 530/350; 536/23.72
[58] Field of Search .......................... 536/23.72

[56] References Cited

U.S. PATENT DOCUMENTS 5,350,671  9/1994  Houghton et al. ................. 435/5

OTHER PUBLICATIONS

Koshy et al., Evaluation of hepatitis C virus protein epitopes for vaccine development, Trends in Biotechnology 14(10):364–369, 1996.

Okamoto et al., Enzyme–Linked Immunosorbent Assay for Antibodies against the Capsid Protein of Hepatitis C Virus with a Synthetic Oligopeptide, Japan. J. Exp. Med. 60(4):223–233, 1990.

Takeuchi et al., Nucleotide sequence of core and envelope genes of the hepatitis C virus genome derived directly from human healthy carriers, Nucl. Acids Res. 18(15):4626, 1990.

*Primary Examiner*—Donna C. Wortman
*Attorney, Agent, or Firm*—Fulbright & Jaworski, LLP

[57] ABSTRACT

The cloning and sequencing of different polypeptides from the genome of a hepatitis C virus is disclosed. The polypeptides are prepared as non-fusion proteins in good yield. The polypeptide originating from the structure protein (core) is soluble under physiological conditions. Since the polypeptides have no foreign protein portions, they are preferably used in test kits and as vaccine.

13 Claims, 8 Drawing Sheets

FIG. 1

```
Met Ser Thr Asn Pro Lys Pro Gln Arg Lys Thr Lys Arg Asn Thr
Asn Arg Arg Pro Gln Asp Val Lys Phe Pro Gly Gly Gln Ile
Val Gly Gly Val Tyr Leu Leu Pro Arg Arg Gly Pro Arg Leu Gly
Val Arg Ala Pro Arg Lys Thr Ser Glu Arg Ser Gln Pro Arg Gly
Arg Arg Gln Pro Ile Pro Lys Ala Arg Arg Pro Glu Gly Arg Thr
Trp Ala Gln Pro Gly Tyr Pro Trp Pro Leu Tyr Gly Asn Glu Gly
Cys Gly Trp Ala Gly Trp Leu Leu Ser Pro Arg Gly Ser Arg Pro
Ser Trp Gly Pro Thr Asp Pro Arg Arg Arg Ser Arg Asn Leu Gly
Lys Val Ile Asp Thr Leu Thr Cys Gly Phe Ala Asp Leu Met Gly
Tyr Ile Pro Leu Val Gly Ala Pro Leu Gly Gly Ala Ala Arg Ala
Leu Ala His Gly Val Arg Val Leu Glu Asp Gly Val Asn Tyr Ala
Thr Gly Asn Leu Pro Gly Cys Ser Phe Ser Ile Phe Leu Leu Ala
Leu Leu Ser Lys Leu Thr Ile Pro Ala Ser END
```

FIG. 2

```
ATG AGC ACA AAT CCT AAA CCT CAA AGA AAA ACC AAA CGT AAC ACC
AAC CGT CGC CCA CAG GAC GTC AAG TTC CCG GGT GGC CAG ATC
GTT GGT GGA GTT TAC TTG TTG ACT TCC GAG CGC AGG GGC AGA TTG GGT
GTG CGC GCA CCG AGG AAG ACT TCC GAG CGG TCG CAA CCT CGT GGT
AGA CGT CAG CCT ATC CCC AAG GCA CGT CGG CCC GAG GGC AGA ACC
TGG GCT CAG CCC GGG TAC CCT TGG CTC CTG TAT GGC AAT GAG GGC
TGC GGG TGG GCG GGA CCC ACA GAC CCC CTT CCC CGT GGA TCT CGG CCT
AGC TGG GGA CCC ACA GAC CTT ACG TGC GGC CTT AGG TCG CGC AAT TTG GGT
AAG GTC ATC GAT ACC GTC GGC GCT CCT CTT GGA TTC GCC GAC CTC ATG GGG
TAC ATA CCG CTC GTC CGG GTT CTG GAA GAC GGC GTG AAC TAT GCA
CTG GCG CAC GGC GTC CCT GGT TGC TCT TTC TCT ATC TTC CTT CTG GCC
ACA GGG AAC CTT CCT GGT TGC TCT TTC TCT ATC TTC CTT CTG GCC
CTG CTC TCT TGC TTG ACC ATC CCC GCT TCC TAA
```

FIG. 3

```
ATG AGC ACA AAT CCT AAA CCT CAA AGA AAA ACC AAA CGT AAC ACC
Met Ser Thr Asn Pro Lys Pro Gln Arg Lys Thr Lys Arg Asn Thr

AAC CGT CGC CCA CAG GAC GTC AAG TTC CCG GGT GGC GGT CAG ATC
Asn Arg Arg Pro Gln Asp Val Lys Phe Pro Gly Gly Gly Gln Ile

GTT GGT GGA GTT TAC TTG TTG AGG CGC AGG CCT AGA TTG GGT
Val Gly Gly Val Tyr Leu Leu Pro Arg Arg Gly Pro Arg Leu Gly

GTG CGC GCA CCG AGG AAG ACT TCC GAG CAA CGG TCG CCT CGT GGT
Val Arg Ala Pro Arg Lys Thr Ser Glu Gln Arg Ser Pro Arg Gly

AGA CGT CAG CCT ATC CCC AAG GCA CGT CGG CGG GAG GGC AGA ACC
Arg Arg Gln Pro Ile Pro Lys Ala Arg Arg Arg Glu Gly Arg Thr

TGG GCT CAG CCC TAC TAT CCT TGG CTC CCC TAT GCC AAT GAG GGC
Trp Ala Gln Pro Tyr Tyr Pro Trp Leu Pro Tyr Gly Asn Glu Gly

TGC GGG TGG GGA GGA GAC CTC TCT GGA CGT TCT CGG CCT
Cys Gly Trp Gly Gly Asp Leu Ser Pro Arg Gly Ser Arg Pro

AGC TGG GGA CCC ACA CCC ACG CGG TGC CGT AGG TCG CGC AAT TTG GGT
Ser Trp Gly Pro Thr Pro Arg Cys Arg Arg Ser Arg Asn Leu Gly

AAG GTC ATC GAT ACC CTT GGC TTC GAC CTC ATG GGG
Lys Val Ile Asp Thr Leu Gly Phe Asp Leu Met Gly

TAC ATA CCG CTC GTC GCT CCT CTT GGA GGA GCT GCC GCC
Tyr Ile Pro Leu Val Ala Pro Leu Gly Gly Ala Ala Ala

CTG GCG CAC GGC GTC CGG GTT CTG GAA GAC GGC GTG AAC TAT GCA
Leu Ala His Gly Val Arg Val Leu Glu Asp Gly Val Asn Tyr Ala

ACA GGG AAC CTT TGC CCT GGT TGC TCT TTC ATC TTC CTT CTG GCC
Thr Gly Asn Leu Cys Pro Gly Cys Ser Phe Ile Phe Leu Leu Ala

CTG CTC TCT TTG ACC ATC CCC GCT TCC TAA
Leu Leu Ser Lys Leu Thr Ile Pro Ala Ser End
```

FIG. 4

```
ATG AGC ACA AAT CCT AAA CCT CAA AGA AAA ACC AAA CGT AAC ACC
Met Ser Thr Asn Pro Lys Pro Gln Arg Lys Thr Lys Arg Asn Thr

AAC CGT CGC CCA CAG GAC GTC AAG TTC CCG GGT GGC GGT CAG ATC
Asn Arg Arg Pro Gln Asp Val Lys Phe Pro Gly Gly Gly Gln Ile

GTT GGA GTT TAC TTG TTG CCG CGC AGG GGC CCT AGA TTG GGT
Val Gly Val Tyr Leu Leu Pro Arg Arg Gly Pro Arg Leu Gly

GTG CGC GCA CCG AGG AAG ACT TCC GAG CGG CAA CCT CGT GGT
Val Arg Ala Pro Arg Lys Thr Ser Glu Arg Gln Pro Arg Gly

AGA CGT CAG CCT ATC CCC AAG GCA CGT CGG CCC GAG GGC AGA ACC
Arg Arg Gln Pro Ile Pro Lys Ala Arg Arg Pro Glu Gly Arg Thr

TGG GCT CAG CCC TAC CCT TGG CTC CCC TAT GGC AAT GAG GGC
Trp Ala Gln Pro Tyr Pro Trp Leu Pro Tyr Gly Asn Glu Gly

TGC GGG TGG GGA TGG CTG CTC TCT CCC CGT GGA TCT CGG CCT
Cys Gly Trp Gly Trp Leu Leu Ser Pro Arg Gly Ser Arg Pro

AGC TGG GGA CCC ACA GAC CCC CGG AGG TCG CGC AAT TTG GGT
Ser Trp Gly Pro Thr Asp Pro Arg Arg Ser Arg Asn Leu Gly

AAG GTC ATC GAT atc tag
Lys Val Ile Asp Ile END
```

FIG. 5

```
atg aga GGA TCC GCT TAC GAA GTG CGC AAC TCC ACG GGG CTT TAC
CAT GTC ACC AAC GAT TGC CCC AAC TCG AGT ATT GTG TAC GAG ACA
GCT GAT GCC ATC CTA CAC GCT CCG GGG TGC GTC CCT TGC GTT CGT
GAG GAT AAC GTC TCG AGG TGT TGG GTG GCG ATG CCC ACG GTG
GCC ACT AGG GAT GGC AAA CTC CCC GCA ACG GAG CTT CGA CGT CAC
ATC GAT CTG GTC GGG AGC GCC ACC CTC TGC TCG GCC CTT TAC
GTG GGG GAC TTG TGC GGG TCT GTC TTT CTT GTC CAG CTG TTT
ACC TTC TCT CCC AGG CGC CAC TGG ACG CAA GAT TGC AAC TGT
TCT ATC TAT CCC GGC CAT ATA ACG CCT ATG CGC ATG GCA TGG GAT
ATG ATG AAC TGG TCC CCT ACG ACG GCA TTG GTA GTA GCT CAG
CTG GTC CGG ATC Cgt cga cct gca gcc aag ctt aat tag
```

FIG. 6

Met Arg Gly Ser Ala Tyr Glu Val Arg Asn Ser Thr Gly Leu Tyr
His Val Thr Asn Asp Cys Pro Asn Ser Ser Ile Val Tyr Glu Thr
Ala Asp Ala Ile Leu His Ala Pro Gly Cys Val Pro Cys Val Arg
Glu Asp Asn Val Ser Arg Cys Trp Val Ala Met Thr Pro Thr Val
Ala Thr Arg Asp Gly Lys Leu Pro Ala Thr Glu Leu Arg Arg His
Ile Asp Leu Leu Val Gly Ser Ala Thr Leu Cys Ser Ala Leu Tyr
Val Gly Asp Leu Cys Gly Ser Val Phe Leu Val Gly Gln Leu Phe
Thr Phe Ser Pro Arg Arg His Trp Thr Thr Gln Asp Cys Asn Cys
Ser Ile Tyr Pro Gly His Ile Thr Gly His Arg Met Ala Trp Asp
Met Met Asn Trp Ser Pro Thr Thr Ala Leu Val Val Ala Gln
Leu Val Arg Ile Arg Arg Pro Ala Ala Lys Leu Asn END

FIG. 7

```
atg aga GGA TCC GCT TAC GAA GTG CGC AAC TCC ACG GGG CTT TAC
Met Arg Gly Ser Ala Tyr Glu Val Arg Asn Ser Thr Gly Leu Tyr CAT GTC ACC AAC GAT TGC CCC AAC TCG AGT ATT GTG TAC GAG ACA
His Val Thr Asn Asp Cys Pro Asn Ser Ser Ile Val Tyr Glu Thr GCT GAT GCC ATC CTA CAC GCT CCG GGG TGC GTC CCT TGC GTT CGT
Ala Asp Ala Ile Leu His Ala Pro Gly Cys Val Pro Cys Val Arg GAG GAT AAC GTC TCG AGG TGT TGG GTG GCG ATG ACC CCC ACG GTG
Glu Asp Asn Val Ser Arg Cys Trp Val Ala Met Thr Pro Thr Val GCC ACT AGG GAT GGC AAA CTC CCC GCA ACG GAG CTT CGA CGT CAC
Ala Thr Arg Asp Gly Lys Leu Pro Ala Thr Glu Leu Arg Arg His ATC GAT CTG CTT GTC GGG AGC GCC ACC CTC TGC TCG GCC CTT TAC
Ile Asp Leu Leu Val Gly Ser Ala Thr Leu Cys Ser Ala Leu Tyr GTG GGG GAC TTG TGC GGG TCT GTC TTT CTT GTC GGT CAG CTG TTT
Val Gly Asp Leu Cys Gly Ser Val Phe Leu Val Gly Gln Leu Phe ACC TTC TCT CCC AGG CGC CAC TGG ACG ACG CAA GAT TGC AAC TGT
Thr Phe Ser Pro Arg Arg His Trp Thr Thr Gln Asp Cys Asn Cys TCT ATC TAT CCC GGC CAT ATA ACG GGT CAC CGC ATG GCA TGG GAT
Ser Ile Tyr Pro Gly His Ile Thr Gly His Arg Met Ala Trp Asp ATG ATG ATG AAC TGG TCC CCT ACG ACG GCA TTG GTA GCT CAG
Met Met Met Asn Trp Ser Pro Thr Thr Ala Leu Val Ala Gln CTG GTC CGG ATC Cgt cga cct gca gcc aag ctt aat tag
Leu Val Arg Ile Arg Arg Pro Ala Ala Lys Leu Asn END
```

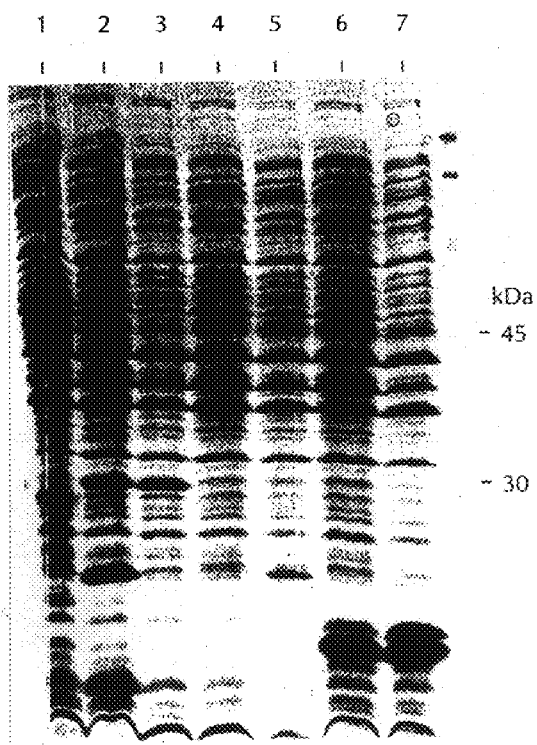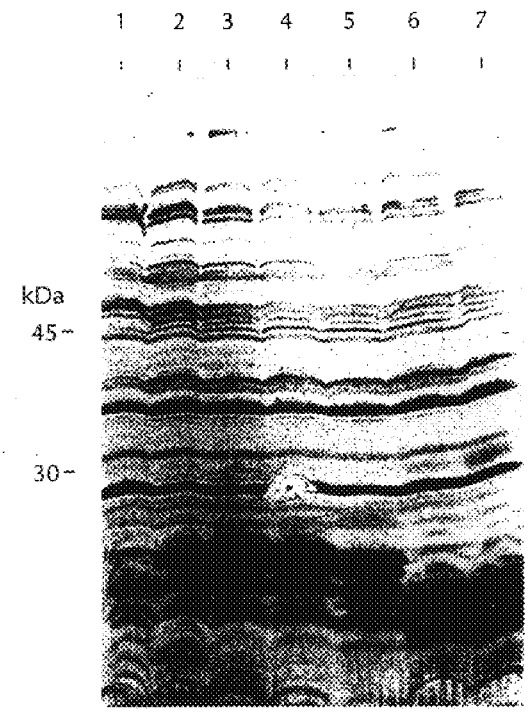
FIG. 8A
FIG. 8B

POLYPEPTIDES DERIVED FROM PROTEINS OF THE HEPATITIS C VIRUS, TEST KITS CONTAINING THESE POLYPEPTIDES AND VACCINES AGAINST INFECTIONS OF HEPATITIS C VIRUSES

It has been known for about 15 years that, aside from hepatitis A and hepatitis B, there are additional hepatitides which, in ignorance of the pathogen, were referred to as non-A-non-B-hepatitis. It has meanwhile been assumed that this group of non-A-non-B-hepatitides is caused by at least two different viruses, which are referred to as hepatitis C or E.

The hepatitis C virus is a single-stranded, encapsulated RNA virus with a diameter of about 50–60 nm. The genome consists of about 10,000 nucleotides and it is possible to differentiate between gene regions, which code for structural proteins such as the envelope and the core protein. Such structural proteins can be called C or core, E or envelope and NS. Moreover, the genome comprises the genes for non-structural components of the virus, such as enzymes, etc. Until now, it was known that the genome comprises different proteins; however, the individual, viral proteins are hardly known (Schweizer Medizinische Wochenschrift (1990), vol. 120, pages 117–124).

A partial nucleotide sequence of the hepatitis C virus was published in the European patent application 88.310922 of the Chiron Corporation. However, it was found out that the nucleotide sequence disclosed there codes only for the so-called non-structural proteins. That part of the nucleotide sequence, which codes for the structural proteins, is not disclosed in this reference.

Further DNA sequences of a non-A-non-B-hepatitis virus antigen are disclosed in European patent application No. 89.309261.9.

The European patent application 90.305421.1 of Chiron Corporation discloses the DNA and amino acid sequence of an HCV virus.

The expression of different HCV virus peptides is known from the state of the art. However, they are always expressed as so-called fusion peptides. The background of the expression as fusion protein is that the hepatitis C virus is adapted to the eukaryotic protein biosynthesis and that therefore it is generally assumed that such polypeptides in bacterial systems, such as the E. coli system, can be expressed only as so-called fusion proteins. The part fused on therefore originates from other proteins, such as the β-galactosidase or the superoxide dismutase. However, it is a disadvantage of such fusion proteins that, when these polypeptides are used for detection reactions, cross reactions can occur with the protein portion fused on and lead to wrongly positive results.

It is therefore an object of the present invention to make polypeptides available, which originate from the hepatitis C virus and can be expressed without a fusion portion but, nevertheless, in good yield.

In the present application, fusion proteins are understood to be those polypeptides, which have a significant proportion of a foreign protein, such as β-galactosidase or superoxide dismutase.

By means of the method disclosed here, it was possible to clone and express polypeptides from the structure proteins C (core) and ENV (envelope). It is important that these polypeptides are parts of structure proteins, which occur in the virus particles at the surface or in regions near the surface. By these means, they come into contact with the immune system and thus bring about an immune response. This immune response is essential, on the one hand, for the detection of an infection, for which it is ascertained whether antibodies to the virus are present and, on the other, for immunization as protection against viral infections.

Preferred polypeptides of the present invention are shown in FIGS. 1, 4 and 6.

By means of the disclosed amino acid sequence, shortened polypeptides, which have the same or comparable immunological properties as the polypeptides described here, can be produced without great difficulty. Likewise, the disclosed amino acid sequences can be altered slightly by exchanging a few amino acids, but so that the immunological properties of the polypeptides are retained. Within the scope of the present invention, those polypeptides are therefore preferred, which represent partial sequences of the disclosed amino acid sequences or differ from the disclosed sequences by the exchange of a few amino acids. The exchanged amino acid sequences should not, however, exceed 2% of the total amino acids.

Furthermore, within the scope of the present invention, three clones are made available, which supply different, defined polypeptides from the genome of the hepatitis C virus.

The serum of a virus-infected patient was the starting material for the preparation of the different clones supplying polypeptides of the hepatitis C virus.

The serum was pretreated by known methods and individual clones were obtained with the help of the polymerase chain reaction (PCR).

The clone NS-3, which has meanwhile been deposited with the German Collection of Microorganisms (DSM), contains the genetic information for a polypeptide of 527 amino acids. At the N terminal of the polypeptide produced by the clone NS-3, there are some amino acids, which have come about due to the cloning and originate from the vector (pUC). These few nonsense amino acids do not, however, represent a fusion portion. The cloned polypeptide has meanwhile been sequenced partially and has the following partial sequence at the C terminal SEQ ID NO: 10:

```
CC  CTC ATG ACC GGC TAT ACC GGC GAC TTC GAC TCG GTG ATA GAC
    LEU MET THR GLY TYR THR GLY ASP PHE ASP SER VAL ILE ASP

TGC AAC ACG TGT GTC ACT CAG ACA GTC GAT TTC AGC CTT GAC CCT
CYS ASN THR CYS VAL TRR GLN THR VAL ASP PHE SER LEU ASP PRO

ACC TTC ACC ATT GAG ACG ACC ACA CTT CCC CAG GAT GCT GTC TCC
TER PHE THR ILE GLU TER THR TER LEU PRO GLN ASP ALA VAL SER

CGC ACT CAA CGA CGG GGC AGG ACT GGC AGG GGG AJG CCG GGC ATC
ARG THR GLN ARG ARG GLY ARG THR GLY ARG GLY LYS PRO GLY ILE

TAC AGA TTT GTG GCA CCG GGG GAA CGC CCC TCC GGC ATG TTC GAC
```

```
                                    -continued
TYR ARG PHE VAL ALA PRO GLY GLU ARG PRO SER GLY MET PHE ASP TCG TCC GTC CTC TGT GAG TGC TAT GAC GCA GGT TGT GCT TGG TAT
SER SER VAL LEU CYS GLU CYS TYR ASP ALA GLY CYS ALA TRP TYR

GAG CTC ACG CCC GCC GAG TGA ATTCAAGCTT
GLU LEU THR PRO ALA GLU STOP
```

The clone NS-4 contains the genetic information for a polypeptide of 247 amino acids and was deposited with the DSM under the number 6848. The polypeptide of the hepatitis C virus, which can be prepared with the help of the clone NS-4, also contains some amino acids at the N terminal, which originated from the pUC vector and also do not represent a fusion portion within the meaning of a foreign protein that has been fused on.

The clone pIC19 H-N512 was deposited with the DSM under the number 6849. The clone pIC19H-N512 contains the information for a polypeptide of the hepatitis C virus, which has 392 amino acids. Here also, there are some amino acids present at the N terminal, which originate from the pUC vector. This HCV-specific peptide has the following amino acid sequence at the N terminal, coded by the also listed DNA sequence SEQ ID NO: 9:

The complex, formed from the inventive polypeptide and the antibody directed against it, is detected by a receptor such as an indicator component. Preferably, the latter is an antibody, which is directed against the antibody that is to be detected. This anti-antibody usually is labeled, which permits detection. The labeling can be, for example, radioactive labeling or labeling with an enzyme, which catalyzes a color reaction.

Within the scope of the present invention, two embodiments of test kits are particularly preferred. The one embodiment, which is also referred to as strip ELISA, is a test kit in the form of a test strip. This test strip has various proteins acting as antigens. Their arrangement is similar to that of a Western Blot. The strips contain at least one inventive polypeptide and, additionally, one or several control proteins, which contribute to evaluating the intensity of the antigen-antibody reaction.

```
ATC CCC TTT GTG TCC TGC CAG CGC GGG TAT AGG GGG GCC TGG CGA
ILE PRO PHE VAL SER CYS GLN ARG GLY TYR ARG GLY ALA TRP ARG

GGG GAC GGC ATC ATG CAC ACT CGC TGC CAC TGT GGA GCT GAG ATC
GLY ASP GLY ILE MET HIS THR ARG CYS HIS CYS GLY ALA GLU ILE

ACC GGA CAT GTC AAG AAC GGG ACG ATG AGG ATC GTC GGT CCT AAG
THR GLY HIS VAL LYS ASN GLY THR MET ARG ILE VAL GLY PRO LYS

ACC TGC AGG AAC ATG TGG AGT GGG ACC TTC CCC ATT AAT GCC TAC
THR CYS ARG ASN MET TRP SER GLY THR PHE PRO ILE ASN ALA TYR

ACC ACG GGC CCC TGT ACC CCC CTT CCT GCG CCG AAC TAT
THR THR GLY PRO CYS THR PRO LEU PRO ALA PRO ASN TYR
```

The polypeptides, disclosed within the scope of the present application, have the advantage that they can be expressed in good yield (about 5% of the total protein) and that this expression is possible without fusing a foreign protein to the polypeptides.

Surprisingly, it has furthermore been found that the inventive polypeptide, originating from the structure protein (core), is soluble under physiological conditions. In this connection, soluble under physiological conditions is understood to mean, for example, soluble in Tris buffers or phosphate buffers, which contain about 0.5 M NaCl.

The solubility of polypeptides plays an important role, if the polypeptides are used in so-called "capture" tests, in which an anti-antibody is bound to the solid phase, the serum to be investigated can react with the solid phase and the antigen is then added in dissolved form. The antigen usually is labeled, which permits the detection of antibodies directed against the antigen.

The polypeptides, produced pursuant to the invention, find use particularly in test kits, which are suitable for the detection of antibodies, which are directed against the hepatitis C virus. A test kit is understood to be an arrangement, which has, as essential component, at least one inventive polypeptide. The polypeptide is usually bound to a solid phase, which is brought into contact with the sample that is to be investigated. The sample to be investigated usually is a serum sample; however, the detection can also be carried out in other antibody-containing biological fluids.

In a preferred method, the polypeptides or proteins are separated electrophoretically and then transferred to the test strip. In a particular preferred embodiment, the polypeptides or proteins are transferred to a nitrocellulose filter, which is then cut into strips.

The test is carried out and evaluated similarly to the well-known ELISA test and the well-known Western Blot.

To begin with, the appropriate proteins or polypeptides are applied on a test strip and bound to the solid surface. This test strip is then incubated with the sample in a dilution buffer. After a sufficiently long period of incubation, the test strip is washed and the indicator component is added. The latter usually is an anti-antibody, to which a color-producing enzyme is coupled. An example of an enzyme catalyzing such a color reaction is peroxidase. After the washing is repeated, substrate, that is, a compound that can be reacted by the enzyme, is added and incubated. Whether antibodies are present can then be read by the color reaction that does or does not take place.

A further preferred embodiment of the inventive test kit is the ELISA test kit. In the case of this test kit, at least one inventive polypeptide is bound to the solid phase of microtiter plates. The individual test compartments of the microtiter plate are incubated with the fluid containing the antibody that is to be detected. After various washing steps, the indicator component is then added and washing is once more carried out. After addition of the substrate, it is then possible to judge by means of the color reaction whether antibodies to the hepatitis C viruses are present.

A further area of application of the inventive polypeptides is the preparation of vaccines. For this, the inventive polypeptides or shorter polypeptides originating from these can, to begin with, be produced in high purity by genetic engineering. The polypeptides are then brought into the form of injectable fluids, which can either be solutions or suspensions. The polypeptides can also be emulsified or enclosed in liposomes. Further components of the vaccines are, for example, water, salt solutions, glucose or glycerin. Moreover, the vaccines contain small amounts of inactive ingredients such as emulsifiers, materials to buffer the pH and, optionally adjuvants, which increase the immune response. As adjuvants, aluminum hydroxide, N-acetyl-muramyl-L-threonyl-D-isoglutamine and similar known compounds can be named. The vaccines are usually applied parenterally by injection, preferably by subcutaneous or intramuscular injection.

Within the scope of the present invention, it has turned out to be advantageous that the claimed polypeptides can be expressed in high yield. In this connection, it is important that the polypeptides are not present as fusion proteins. Proteins which cannot readily be prepared by genetic engineering are usually expressed in the form of fusion proteins, the desired proteins or polypeptides being fused to other, generally bacterial proteins, which can be expressed well. A so-called fusion protein is then obtained. It contains a protein portion that is fused on and the desired polypeptide or protein, the two parts being fused together to a so-called fusion protein.

Particularly, however, for immunological detection methods or the preparation of vaccines is the preparation of the desired polypeptides as fusion protein undesirable, since the possibility cannot be excluded that there are also antibodies against the protein portion that is fused on and that these antibodies simulate antibodies against the viral antigen in the immunological detection method in those cases where, in actual fact, only antibodies against the protein portion that has been fused on are present.

For immunization with vaccines, it is also not desirable that the protein or polypeptide, against which antibodies are to be produced, has an impurity with a different protein or protein portion, since in this case also antibodies are formed against this component. Within the scope of the present invention, it has been possible to prepare the inventive polypeptides in pure form. The inventive polypeptides have, at most, 15 amino acids, which originate from other genes, with which the gene for the inventive polypeptides was brought into contact within the scope of the cloning or expressing. It is, however, particularly preferred if the inventive polypeptides contain fewer than 5 amino acids, which originate from artifacts going back to the cloning.

BRIEF DESCRIPTION OF THE FIGURES

FIG. 1: The amino acid sequence of the HCV-core-coding region (C-2) is shown.

FIG. 2: The nucleic acid sequence of the HCV-core-coding region (C-1).

FIG. 3: The correlation between the nucleic acid sequence and the amino acid sequence of HCV-core-coding region (C-1) is shown.

FIG. 4: The nucleic acid sequence and amino acid sequence of the shortened HCV-core-coding region is shown, which has the amino acid sequence 1–123 and corresponds to an expression product with approximately 15 kD.

FIG. 5: The nucleic acid sequence of the ENV (envelope)-coding region of the hepatitis C virus (HCV) is shown, the nucleotides, written with lowercase letters, originating from the sequences of the vector, and also being translated.

FIG. 6: The amino acid sequence of the ENV (envelope) polypeptide of the hepatitis C virus is shown.

FIG. 7: A correlation is shown between the nucleic acid sequence and the amino acid sequence of the ENV (envelope) of the polypeptide region of hepatitis C virus. The nucleotide sequences, written with lower case letters, originate from the sequences of the vector and are also translated during the expression.

FIG. 8: The gels, described in Example 2, are shown.

EXAMPLE 1

Producing the Sequences Coding for HCV-CORE and ENV-1

Starting from the known sequence (European patent application 88310922), DNA primers were synthesized, which serve, in the case of a c-DNA synthesis, as the starting material in the direction of the 5' end of the viral genome, as well as a primer, which lies at the 5' end of the c-DNA primer and is used as a hybridization specimen.

The primer for the c-DNA synthesis has the following sequence SEQ ID NO: 10:

5'-GGGAGTGAAGCAATATACCGGACC 3'

For the hybridization:

5'-CCGATTTTGACCAGGGCTGGGGCCCTATCAGT TAT 3' SEQ ID NO: 11

Plasma (5 mL) of a chronically HCV-infected patient were added to a 20% sucrose cushion and centrifuged for 2 hours at 100,000 g. The pellet was resuspended in 300 μL buffer with 20 mM tris-HCl having a pH of 8.0, 200 mM NaCl, 10 mM EDTA, 2% SDS and 1 mg/mL of proteinase K and incubated for 1.5 hours at 55° C. After phenyl/chloroform treatment, nucleic acids were then precipitated with ethanol and subsequently taken up again in 50 μL of water.

The RNA of this solution was reversely transcribed with the primer given above by the usual methods and inserted in a lambda gt11 phage. HCV-DNA-positive clones were found by hybridizing with the hybridizing primer. For this purpose, this primer was labeled at the ends with digoxygenin-labeled UTP and terminal transferase at the ends. The bound primer was then detected with a commercial kit (Boehringer Mannheim).

Hybridization-positive phages were tested for the size of their HCV insert by means of restriction digestion. A clone with an insert of 1.7 kb was subcloned in a pUC8 vector and the sequence was determined. Starting out from commercial pUC sequencing primers, the sequence of the insert ends was determined first; subsequently, primers with sequences of the newly determined 3' ends were synthesized and then used for the next sequencing reaction. The sequence, so determined, results in a continuous reading frame, which commences 169 nucleotides from the start of the insert.

In the case of HCV, the coding regions of the core or the capsid protein, as well as the two regions for membrane proteins adjoining thereon lie at the start of the polyprotein.

The region of the core protein as well as of the membrane protein that follows directly was subcloned for expression in E. coli. This was done by means of specific DNA primers and PCR (polymerase chain reaction). For this, the region of the DNA coding for the protein is amplified.

The primer sequences, which served to amplify the DNA region, which was subsequently cloned and led to the expression of core protein were:

5'-gagggatccatc ATG AGC ACA AAT CCT AAA CC SEQ ID NO: 12 for the 5' end

5'-gagaagctta GGA AGC GGG GAT GGT TCA AGc SEQ ID NO: 13 for the 3' end

The primer sequences, which served for the amplification of the DNA region, which was subsequently cloned and led to the expression of ENV-1 protein were:

gagggatcc GCT TAC GGA GTG CGC AAC SEQ ID NO: 14 for the 5' end gagGGATCC GGA CCA GCT TGA GCT ACT AC SEQ ID NO: 15 for the 3' end Nucleotides which are not capitalized are not HCV-specific; they are used in primers, in order to have restriction sites (GGATCC-BamHI, AAGCTT-HindIII, TCATGA-BspHII) available for the subsequent cloning.

The amplified DNA fragments (463 nucleotides for ENV-1, 579 nucleotides for core), obtained from the PCR, were cut with BamHI (ENV-1) or BamHI and HindIII (core) and inserted in pUC8.

An *E. coli* clone with the plasmid pUC8-ENV-1 with the coding region of the ENV-1 expresses after IPTG induction a protein about 25 kDal in size in an amount, which permits efficient purification by conventional methods (molecular sieve chromatography, ion exchange chromatography). pUC8-C1 with the core-coding region is produced in a lesser amount; shifting the insert into a different expression vector (pDS, pKK233-2) does not bring about any significant improvement. However, after the insert was shortened starting from the 3' end, there was a very good expression in the *E. coli* cells; the expression product with about 15 kdal corresponds to the core sequence of amino acids 1 to 124. This antigen can also be purified very efficiently with conventional methods.

EXAMPLE 2

Expression and Immune Reaction of the "core" and "env1" HCV Proteins

*Escherichia coli* cells with the appropriate expression plasmids were cultured in a liquid culture and, upon reaching an optical density (600 nm) of 0.7 induced with 2 mM IPTG (isopropyl-β-thiogalactoside) for 3 hours. The cell pellet of 1.5 mL culture was subsequently resuspended in 300 μL of 2% SDS, 5% mercaptoethanol, 20 mM tris-HCl having a pH of 7.5, 2% bromphenol blue and 30% sucrose and incubated at 5 minutes at 100° C. The proteins are separated on a 17.5% SDS-polyacrylamide gel (cross-linked DADT). The gels are shown in FIG. 8.

The picture at the left shows this gel after the proteins are stained with Coomassie blue, the one at the right showing it after immune staining. For this purpose, the separated proteins were transferred by "Western Blotting" to a nitrocellulose membrane. The membrane was subsequently incubated with an HCV-positive serum in a dilution of 1:100 with TFBS (146 g NaCl, 100 mL of 1 M tris-HCl of pH 7.5, 0.5 mL of Tween-20) for 4 hours and unbound antibodies were removed by washing three times for 5 minutes with TTBS. Bound antibodies were detected by incubating for 1 hour with a peroxidase-conjugated anti-human-IgG rabbit antibody, washing with TTBS and staining with diaminobenzidine and peroxide. Weaker bands, which occur in each lane, result from anti-*E. coli* antibodies of the HCV serum used.

Between the two Figures, the distances traveled by proteins 45 and 30 KDal in size are given as molecular weight standards.

The individual lanes of the gel were loaded with:

lane 1: pUC8, control.

lane 2: pDS-ENV-1, expression of the HCV-ENV-1 with a size of about 25 kdal.

lane 3: pUC8-C1. Expression of the core, amino acids 1–190, size approximately 26 kdal, 20 amino acids are still fused on due to cloning steps.

lane 4: pDS-C1, like trace 3; however the product is smaller since fewer amino acids are fused on.

lane 5: pKK-C1, like traces 3 and 4; the product here consists only of HCV specific amino acids; the sequence is given in the Figures.

lane 6: pDS-C1Cla, abbreviated core product, from amino acid 1 to 124, 2 foreign amino acids are still fused to the N terminal and 1 to the C terminal.

lane 7: pKK-C1-Cla, like trace 6, however, with authentic HCV-N terminal, a foreign amino acid at the C terminal, sequence is given in the Figures.

The ENV-1 product is expressed in a relatively large amount. However, it reacts only very weakly in the immunoblot with the serum of a chronically infected person tested here. The core products all react very strongly; a much improved expression yield can be obtained by shortening the reading frame from the direction of the C terminal up to amino acid 124.

EXAMPLE 3

Testing the Reactivity of Core and ENV-1

To determine the reactivity of antibodies in patient sera with these proteins, the two purified antigens were separated next to one another on 17.5% SDS polyacrylamide gels and transferred to nitrocellulose. The nitrocellulose membrane was now cut into narrow strips, so that in each case both traces with ENV-1 and core were on one strip. The strips were now incubated with serum from different patients and specific antibodies were detected by means of immune staining.

First Test:

22 sera from patients with increased transaminase values, all HCV-ELISA with non-structure proteins negative;

1 serum reactive with core

Second Test:

9 sera from patients with increased transaminase values, HCV-ELISA with non-structure proteins borderline;

2 sera reactive with core

Third Test:

4 sera from hepatitis patients with autoimmune reactivity, all HCV-ELISA with non-structure proteins positive;

3 sera reactive with core.

The Examples show that test kits with the inventive polypeptides are more sensitive (Tests 1 and 2) as well as more specific (Test 3) than test kits, in which non-structure proteins are used.

EXAMPLE 4

The polypeptide shown in FIG. 4 (core antigen) was shortened further at the C-terminal end. This was done by means of PCR from the core-coding plasmid (Example 1), the 5'-PCR core primer from Example 1, as well as a 3'-primer with the following sequence SEQ ID NO: 16:

c gga agc tta CCT ACG CCG GGG GTC TGT GGG

This primer hybridizes on the core-coding plasmid up to a nucleic acid sequence, which corresponds to the amino acid 115 of the core peptide. A codon for the translation step, as well as a HindIII site for the cloning in pUC8/pKK233-2 follow, as in Example 1.

The polypeptide has the amino acid sequence shown in FIG. 4 which, however, contrary to FIG. 4, ends after the 3 arginine groups in the last line but one of FIG. 4.

This polypeptide can be expressed and purified particularly readily.

This polypeptide can be purified by initially awaiting the formation of so-called inclusion bodies and then lysing the cells. The pellet is taken up in 8 M urea and transferred to a DEAE column (8 M urea, pH of 8.8). Elution from the DEAE column is accomplished with a salt gradient, the positive fractions being passed through a Q-sepharose column at a pH of 8.0. The active fractions pass through the column and are furthermore passed through an S-sepharose column at a pH of 7.7. The polypeptide is then eluted at a salt concentration of 0.4 M NaCl. The polypeptide obtained can then be dialyzed against tris buffer, which contains 0.5 M NaCl.

EXAMPLE 5

The clone pIC19 H-N512, deposited with the DSM under the number 6849, was obtained in the following manner. As described above, the serum of a patient infected with the hepatitis C virus was treated and the viral RNA was amplified with the help of the PCR method. To begin with, a first pre-clone was then produced, which had an insert of about 617 nucleotides. The following primers were used for the synthesis:

5'-primer SEQ ID NO: 17:

CTGCCTGGGATCCCCTTTGTGTCC and

3'-primer SEQ ID NO: 18

GGAAAGCTTAAGCGGATAGCTGGCTAGCCGAGGAG.

The restriction enzyme BamHI/HindIII was used for the cloning. The 3' end of this clone contains an NheI restriction site (GCT AGC) before the HindIII restriction site.

In a similar manner, a further pre-clone was synthesized, which contained an insert of about 615 nucleotides. The following primers were used here:

5'-primer SEQ ID NO: 19:

GAGGGATCCAGGGGATCACCCCCCTCTGTGGCC;

3'-primer SEQ ID NO: 20:

GAGAAGCTTGAATTCTATGTGACTTTCT-TCTGCCTTTGGCAAG.

The 5' end of this clone (cloned with BamHI/HindIII) is overlapped with the first pre-clone and also contains the NheI restriction site.

The inserts of the two pre-clones were assembled by re-cloning using the NheI restriction site, the above-mentioned clone pIC19H-N512 being obtained. The hepatitis C-specific DNA insert was sequenced on and the following partial sequence SEQ ID NO: 19 (DNA and amino acid) was determined at the N terminal:

```
ATC CCC TTT GTG TCC TGC CAG CGC GGG TAT AGG GGG GCC TGG CGA
ILE PRO PHE VAL SER CYS GLN ARG GLY TYR ARG GLY ALA TRP ARG

GGG GAC GGC ATC ATG CAC ACT CGC TGC CAC TGT GGA GCT GAG ATC
GLY ASP GLY ILE MET HIS THR ARG CYS HIS CYS GLY ALA GLU ILE

ACC GGA CAT GTC AAG AAC GGG ACG ATG AGG ATC GTC GGT CCT AAG
THR GLY HIS VAL LYS ASN GLY THR MET ARG ILE VAL GLY PRO LYS

ACC TGC AGG AAC ATG TGG AGT GGG ACC TTC CCC ATT AAT GCC TAC
THR CYS ARG ASN MET TRP SER GLY THR PHE PRO ILE ASN ALA TYR

ACC ACG GGC CCC TGT ACC CCC CTT CCT GCG CCG AAC TAT
THR THR GLY PRO CYS THR PRO LEU PRO ALA PRO ASN TYR
```

EXAMPLE 6

Clone NS-3, which codes for a viral polypeptide of 527 amino acids, was deposited with the DSM under the number 6847. At the N terminal, the polypeptide still has some amino acids, which originate from the cloning vector pUC, but represent so-called nonsense amino acids.

Here also, in a manner analogous to Example 5, two overlapping pre-clones were prepared, the clone inserts then being combined with one another. The following primers were used to prepare the one pre-clone, which had an insert of 815 nucleotides:

5'-primer SEQ ID NO: 21:

AAGGGATCCGGCCGGGAGATACTGCTCGGG;

3'-primer SEQ ID NO: 22:

GGCAAGCTTGAATTCAGATGTTAGGATC-GATCCCATGAG.

The restriction endonucleases BamHI/HindIII were used here for the cloning. The second pre-clone had an insert of 791 nucleotides. This clone was obtained by using the following primer:

5'-primer SEQ ID NO: 23:

GGAGGATCCGCTCATGGGATCGATCCTAAC and

3'-primer SEQ ID NO: 24:

GGAAGCTTGAATTCACTCGGCGGGCGT-GAGCTCATACCAAG.

Here also, cloning was carried out with the restriction endonuclease restriction sites BamHI/HindIII. The two clones were assembled over a singular ClaI restriction site (ATC GAT), which was localized at the 3' end for the first pre-clone and at the 5' prime end for the second pre-clone. A partial sequence of this clone was determined, starting from the C terminal of the virus-specific polypeptide, the following DNA and amino sequence being determined SEQ ID NO: 10:

```
CC CTC ATG ACC GGC TAT ACC GGC GAC TTC GAC TCG GTG ATA GAC
   LEU MET THR GLY TYR THR GLY ASP PHE ASP SER VAL ILE ASP

TGC AAC ACG TGT GTC ACT CAG ACA GTC GAT TTC AGC CTT GAC CCT
CYS ASN THR CYS VAL TRR GLN THR VAL ASP PHE SER LEU ASP PRO

ACC TTC ACC ATT GAG ACG ACC ACA CTT CCC CAG GAT GCT GTC TCC
TER PHE THR ILE GLU TER THR TER LEU PRO GLN ASP ALA VAL SER

CGC ACT CAA CGA CGG GGC AGG ACT GGC AGG GGG AJG CCG GGC ATC
ARG THR GLN ARG ARG GLY ARG THR GLY ARG GLY LYS PRO GLY ILE

TAC AGA TTT GTG GCA CCG GGG GAA CGC CCC TCC GGC ATG TTC GAC
TYR ARG PHE VAL ALA PRO GLY GLU ARG PRO SER GLY MET PHE ASP

TCG TCC GTC CTC TGT GAG TGC TAT GAC GCA GGT TGT GCT TGG TAT
SER SER VAL LEU CYS GLU CYS TYR ASP ALA GLY CYS ALA TRP TYR

GAG CTC ACG CCC GCC GAG TGA ATTCAAGCTT
GLU LEU THR PRO ALA GLU STOP
```

EXAMPLE 7

Clone NS-4, which has meanwhile been deposited with the DSM under the number 6848, codes for a polypeptide of 247 amino acids, which originates from a viral protein. This polypeptide also has some amino acids at the N terminal, which originate from the vector pUC and code for so-called nonsense amino acids. This clone was prepared by the methods described above, using the following primer:

5'-primer SEQ ID NO: 25:
   GGAGGATCCCCCACCCTCCATGGGCCAA-CACCCC;
3'-primer SEQ ID NO: 26:
   GGGAAGCTTGAATTCAAAGAGCTCCCGC-CACGCCCGC.

This PCR fragment was cloned by means of BamHI (5' end) and HindIII (3' end) in pUC8.

---

What is claimed is:

1. An isolated soluble polypeptide prepared by genetic engineering wherein said soluble polypeptide consists of an amino acid sequence selected from the group consisting of SEQ ID NO: 4, amino acids 1–124 of SEQ ID NO: 4 and amino acids 1–115 of SEQ ID NO: 4.

2. An isolated soluble polypeptide prepared by genetic engineering wherein said soluble polypeptide consists of an amino acid sequence selected from the group consisting of (i) SEQ ID NO: 4 linked to an amino acid sequence consisting of 1–15 amino acids wherein said 1–15 amino acids are linked to the N terminal of SEQ ID NO: 4, (ii) SEQ ID NO: 4 linked to an amino acid sequence consisting of 1–15 amino acids wherein said 1–15 amino acids are linked to the C terminal of SEQ ID NO: 4, (iii) the sequence of amino acids 1–124 of SEQ ID NO: 4 linked to an amino acid sequence consisting of 1–15 amino acids wherein said 1–15 amino acids are linked to the N terminal of the sequence of amino acids 1–124 of SEQ ID NO: 4, (iv) the sequence of amino acids 1–124 of SEQ ID NO: 4 linked to an amino acid sequence consisting of 1–15 amino acids wherein said 1–15 amino acids are linked to the C terminal of the sequence of amino acids of 1–124 of SEQ ID NO: 4, (v) the sequence of amino acids 1–115 of SEQ ID NO: 4 linked to an amino acid sequence consisting of 1–15 amino acids wherein said 1–15 amino acids are linked to the N terminal of the sequence of amino acids 1–115 of SEQ ID NO: 4, and (vi) the sequence of amino acids 1–115 of SEQ ID NO: 4 linked to an amino acid sequence consisting of 1–15 amino acids wherein said 1–15 amino acids are linked to the C terminal of the sequence of amino acids 1–115 of SEQ ID NO: 4, (vii) SEQ ID NO: 4 linked to a first amino acid sequence consisting of 1–15 amino acids and a second amino aid sequence consisting of 1–15 amino acids, wherein said first amino acid sequence is linked to the N-terminus of SEQ ID NO: 4 and said second amino acid sequence is linked to the C terminus of SEQ ID NQ: 4 and wherein said first and second amino acid sequences may be the same or different, (viii) the sequence of amino acids 1–124 of SEQ ID NO: 4 linked to a first amino acid sequence consisting of 1–15 amino acids and a second amino aid sequence consisting of 1–15 amino acids, wherein said first amino acid sequence is linked to the N-terminus of SEQ ID NO: 4 and said second amino acid sequence is linked to the C terminus of SEQ ID NO: 4 and wherein said first and second amino acid sequences may be the same or different, (ix) the sequence of amino acids 1–115 of SEQ ID NO: 4 linked to a first amino acid sequence consisting of 1–15 amino acids and a second amino aid sequence consisting of 1–15 amino acids, wherein said first amino acid sequence is linked to the N-terminus of SEQ ID NO: 4 and said second amino acid sequence is linked to the C terminus of SEQ ID NO: 4 and wherein said first and second amino acid sequences may be the same or different, wherein said isolated polypeptide consists of an amino acid sequence that is not found in naturally occurring hepatitis C virus.

3. An isolated soluble polypeptide prepared by genetic engineering wherein said soluble polypeptide consists of the amino acid sequence of SEQ ID NO: 6.

4. An isolated polypeptide prepared by genetic engineering wherein said polypeptide consists of an amino acid sequence selected from the group consisting of:

(i) SEQ ID NO: 6 linked to an amino acid sequence consisting of 1–15 amino acids wherein said 1–15 amino acids are linked to the N terminus of SEQ ID NO: 6, (ii) SEQ ID NO: 6 linked to an amino acid sequence consisting of 1–15 amino acids wherein said 1–15 amino acids are linked to the C terminus of said SEQ ID NO: 6, and (iii) SEQ ID NO: 6 linked to a first amino acid sequence consisting of 1–15 amino acids and a second amino aid sequence consisting of 1–15 amino acids, wherein said first amino acid sequence is linked to the N-terminus of SEQ ID NO: 6 and said second amino acid sequence is linked to the C terminus of SEQ ID NO: 6 and wherein said first and second amino acid sequences may be the same or different, wherein said isolated polypeptide consists of an amino acid sequence that is not found in naturally occurring hepatitis C virus.

5. The isolated polypeptide of claim 2 or 4, wherein said amino acid sequence consisting of 1–15 amino acids consists of 1–5 amino acids.

6. A test kit useful in determining an antibody which specifically binds to a hepatitis C virus antigen comprising a separate portion of each of (a) the isolated polypeptide of any one of claims 1, 2, 3 or 4 and (b) a receptor which specifically binds to a complex of said isolated polypeptide and said antibody.

7. The test kit of claim 6, wherein said receptor which specifically binds to a complex formed between said polypeptide and said antibody is a labeled receptor.

8. The test kit of claim 7, wherein said receptor is labelled with an enzyme.

9. Test strip usefull in determining an antibody which specifically binds to a hepatitis C virus antigen, comprising a sample of each of (i) an isolated polypeptide selected from the group consisting of the polypeptide of claim 1, the polypeptide of claim 2, the polypeptide of claim 3 and the polypeptide of claim 4, (ii) a control protein, wherein said isolated polypeptide and control protein are bound to a carrier.

10. Method for determining HCV specific antibodies comprising contacting a test sample with the isolated soluble polypeptide of any one of claims 1, 2, 3 or 4 under conditions favoring formation of a complex there between, and determining said complex as a determination of antibodies in said sample.

11. A composition comprising (i) an isolated polypeptide selected from the group consisting of the polypeptide of claim 1, the polypeptide of claim 2, the polypeptide of claim 3 and the polypetide of claim 4, (ii) a pharmaceutically acceptable adjuvant.

12. An isolated polypeptide consisting of the amino acid sequence encoded by a nucleic acid molecule consisting of SEQ ID NO: 7.

13. An isolated nucleic acid molecule which codes for an HCV polypeptide, wherein said nucleic acid molecule has a nucleotide sequence selected from the group consisting of SEQ ID NO: 5 and nucleotides 7–463 of SEQ ID NO: 5.

* * * * *

UNITED STATES PATENT AND TRADEMARK OFFICE
CERTIFICATE OF CORRECTION

PATENT NO. : 6,136,527
DATED : October 24, 2000
INVENTOR(S) : Fuchs, et. al.

It is certified that error appears in the above-identified patent and that said Letters Patent is hereby corrected as shown below:

In column 2, line 5, change "superoxide" to - - peroxide - -.
In column 7, line 56, change "TFBS" to - - TTBS - -.
In column 10, line 11, change "19" to - - 9 - -.

Signed and Sealed this

Twenty-second Day of May, 2001

Attest:

NICHOLAS P. GODICI

Attesting Officer

Acting Director of the United States Patent and Trademark Office

SEQUENCE LISTING

```
(1) GENERAL INFORMATION:

(iii) NUMBER OF SEQUENCES: 26

(2) INFORMATION FOR SEQ ID NO: 1:

(i) SEQUENCE CHARACTERISTICS:
        (A) LENGTH: 190 amino acids
        (B) TYPE: amino acid
        (C) STRANDEDNESS: single
        (D) TOPOLOGY: linear (ii) MOLECULE TYPE: protein (vi) ORIGINAL SOURCE:
         (A) ORGANISM: Hepatitis virus (xi) SEQUENCE DESCRIPTION: SEQ ID NO: 1:

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Pro Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
                100                 105                 110
```

```
    Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
        130                 135                 140

Gly Gly Ala Ala Arg Ala Leu Ala His Gly Val Arg Val Leu Glu Asp
    145                 150                 155                 160

Gly Val Asn Tyr Ala Thr Gly Asn Leu Pro Gly Cys Ser Phe Ser Ile
                    165                 170                 175

Phe Leu Leu Ala Leu Leu Ser Lys Leu Thr Ile Pro Ala Ser
                180                 185                 190

(2) INFORMATION FOR SEQ ID NO: 2:

(i) SEQUENCE CHARACTERISTICS:
        (A) LENGTH: 573 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Hepatitis virus (xi) SEQUENCE DESCRIPTION: SEQ ID NO: 2:

ATGAGCACAA ATCCTAAACC TCAAAGAAAA ACCAAACGTA ACACCAACCG TCGCCCACAG    60

GACGTCAAGT TCCCGGGTGG CGGTCAGATC GTTGGTGGAG TTTACTTGTT GCCGCGCAGG   120

GGCCCTAGAT TGGGTGTGCG CGCACCGAGG AAGACTTCCG AGCGGTCGCA ACCTCGTGGT   180

AGACGTCAGC CTATCCCCAA GGCACGTCGG CCCGAGGGCA GAACCTGGGC TCAGCCCGGG   240

TACCCTTGGC CCCTCTATGG CAATGAGGGC TGCGGGTGGG CGGGATGGCT CCTGTCTCCC   300

CGTGGATCTC GGCCTAGCTG GGGACCCACA GACCCCCGGC GTAGGTCGCG CAATTTGGGT   360

AAGGTCATCG ATACCCTTAC GTGCGGCTTC GCCGACCTCA TGGGGTACAT ACCGCTCGTC   420

GGCGCTCCTC TTGGAGGAGC TGCCAGGGCC CTGGCGCACG GCGTCCGGGT TCTGGAAGAC   480

GGCGTGAACT ATGCAACAGG GAACCTTCCT GGTTGCTCTT TCTCTATCTT CCTTCTGGCC   540

CTGCTCTCTT GCTTGACCAT CCCCGCTTCC TAA                               573

(2) INFORMATION FOR SEQ ID NO: 3:

(i) SEQUENCE CHARACTERISTICS:
        (A) LENGTH: 573 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Hepatitis virus (ix) FEATURE:
        (A) NAME/KEY: CDS
        (B) LOCATION: 1..723

(xi) SEQUENCE DESCRIPTION: SEQ ID NO: 3:

ATG AGC ACA AAT CCT AAA CCT CAA AGA AAA ACC AAA CGT AAC ACC AAC     48
Met Ser Thr Asn Pro Lys Pro Gln Arg Lys Thr Lys Arg Asn Thr Asn
  1               5                  10                  15

CGT CGC CCA CAG GAC GTC AAG TTC CCG GGT GGC GGT CAG ATC GTT GGT     96
Arg Arg Pro Gln Asp Val Lys Phe Pro Gly Gly Gly Gln Ile Val Gly
             20                  25                  30
```

-continued

```
GGA GTT TAC TTG TTG CCG CGC AGG GGC CCT AGA TTG GGT GTG CGC GCA      144
Gly Val Tyr Leu Leu Pro Arg Arg Gly Pro Arg Leu Gly Val Arg Ala
            35                  40                  45

CCG AGG AAG ACT TCC GAG CGG TCG CAA CCT CGT GGT AGA CGT CAG CCT      192
Pro Arg Lys Thr Ser Glu Arg Ser Gln Pro Arg Gly Arg Arg Gln Pro
 50                  55                  60

ATC CCC AAG GCA CGT CGG CCC GAG GGC AGA ACC TGG GCT CAG CCC GGG      240
Ile Pro Lys Ala Arg Arg Pro Glu Gly Arg Thr Trp Ala Gln Pro Gly
 65                  70                  75                  80

TAC CCT TGG CCC CTC TAT GGC AAT GAG GGC TGC GGG TGG GCG GGA TGG      288
Tyr Pro Trp Pro Leu Tyr Gly Asn Glu Gly Cys Gly Trp Ala Gly Trp
                85                  90                  95

CTC CTG TCT CCC CGT GGA TCT CGG CCT AGC TGG GGA CCC ACA GAC CCC      336
Leu Leu Ser Pro Arg Gly Ser Arg Pro Ser Trp Gly Pro Thr Asp Pro
            100                 105                 110

CGG CGT AGG TCG CGC AAT TTG GGT AAG GTC ATC GAT ACC CTT ACG TGC      384
Arg Arg Arg Ser Arg Asn Leu Gly Lys Val Ile Asp Thr Leu Thr Cys
            115                 120                 125

GGC TTC GCC GAC CTC ATG GGG TAC ATA CCG CTC GTC GGC GCT CCT CTT      432
Gly Phe Ala Asp Leu Met Gly Tyr Ile Pro Leu Val Gly Ala Pro Leu
130                 135                 140

GGA GGA GCT GCC AGG GCC CTG GCG CAC GGC GTC CGG GTT CTG GAA GAC      480
Gly Gly Ala Ala Arg Ala Leu Ala His Gly Val Arg Val Leu Glu Asp
145                 150                 155                 160

GGC GTG AAC TAT GCA ACA GGG AAC CTT CCT GGT TGC TCT TTC TCT ATC      528
Gly Val Asn Tyr Ala Thr Gly Asn Leu Pro Gly Cys Ser Phe Ser Ile
                165                 170                 175

TTC CTT CTG GCC CTG CTC TCT TGC TTG ACC ATC CCC GCT TCC TAA          573
Phe Leu Leu Ala Leu Leu Ser Cys Leu Thr Ile Pro Ala Ser
            180                 185                 190
```

(2) INFORMATION FOR SEQ ID NO: 4:

(i) SEQUENCE CHARACTERISTICS:
        (A) LENGTH: 378 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Hepatitis virus (ix) FEATURE:
        (A) NAME/KEY: CDS
        (B) LOCATION: 1..481

(xi) SEQUENCE DESCRIPTION: SEQ ID NO: 4:

```
ATG AGC ACA AAT CCT AAA CCT CAA AGA AAA ACC AAA CGT AAC ACC AAC      48
Met Ser Thr Asn Pro Lys Pro Gln Arg Lys Thr Lys Arg Asn Thr Asn
 1                   5                  10                  15

CGT CGC CCA CAG GAC TGC AAG TTC CCG GGT GGC GGT CAG ATC GTT GGT      96
Arg Arg Pro Gln Asp Cys Lys Phe Pro Gly Gly Gly Gln Ile Val Gly
            20                  25                  30

GGA GTT TAC TTG TTG CCG CGC AGG GGC CCT AGA TTG GGT GTG CGC GCA      144
Gly Val Tyr Leu Leu Pro Arg Arg Gly Pro Arg Leu Gly Val Arg Ala
            35                  40                  45

CCG AGG AAG ACT TCC GAG CGG TCG CAA CCT CGT GGT AGA CGT CAG CCT      192
Pro Arg Lys Thr Ser Glu Arg Ser Gln Pro Arg Gly Arg Arg Gln Pro
 50                  55                  60

ATC CCC AAG GCA CGT CGG CCC GAG GGC AGA ACC TGG GCT CAG CCC GGG      240
Ile Pro Lys Ala Arg Arg Pro Glu Gly Arg Thr Trp Ala Gln Pro Gly
```

```
                65                    70                   75                    80
            TAC CCT TGG CCC CTC TAT GGC AAT GAG GGC TGC GGG TGG GCG GGA TGG        288
            Tyr Pro Trp Pro Leu Tyr Gly Asn Glu Gly Cys Gly Trp Ala Gly Trp
                                85                  90                 95

CTC CTG TCT CCC CGT GGA TCT CGG CCT AGC TGG GGA CCC ACA GAC CCC        336
            Leu Leu Ser Pro Arg Gly Ser Arg Pro Ser Trp Gly Pro Thr Asp Pro
                            100                 105                 110

CGG CGT AGG TCG CGC AAT TTG GGT AAG GTC ATC GAT ATC TAG                378
            Arg Arg Arg Ser Arg Asn Leu Gly Lys Val Ile Asp Ile
                        115                 120                 125

(2) INFORMATION FOR SEQ ID NO: 5:

(i) SEQUENCE CHARACTERISTICS:
        (A) LENGTH: 489 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Hepatitis virus (xi) SEQUENCE DESCRIPTION: SEQ ID NO: 5:

ATGAGAGGAT CCGCTTACGA AGTGCGCAAC TCCACGGGGC TTTACCATGT CACCAACGAT        60

TGCCCCAACT CGAGTATTGT GTACGAGACA GCTGATGCCA TCCTACACGC TCCGGGGTGC       120

GTCCCTTGCG TTCGTGAGGA TAACGTCTCG AGGTGTTGGG TGGCGATGAC CCCCACGGTG       180

GCCACTAGGG ATGGCAAACT CCCCGCAACG GAGCTTCGAC GTCACATCGA TCTGCTTGTC       240

GGGAGCGCCA CCCTCTGCTC GGCCCTTTAC GTGGGGGACT TGTGCGGGTC TGTCTTTCTT       300

GTCGGTCAGC TGTTTACCTT CTCTCCCAGG CGCCACTGGA CGACGCAAGA TTGCAACTGT       360

TCTATCTATC CCGGCCATAT AACGGGTCAC CGCATGGCAT GGGATATGAT GATGAACTGG       420

TCCCCTACGA CGGCATTGGT AGTAGCTCAG CTGGTCCGGA TCCGTCGACC TGCAGCCAAG       480

CTTAATTAG                                                                489

(2) INFORMATION FOR SEQ ID NO: 6:

(i) SEQUENCE CHARACTERISTICS:
        (A) LENGTH: 162 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Hepatitis virus (xi) SEQUENCE DESCRIPTION: SEQ ID NO: 6:

Met Arg Gly Ser Ala Tyr Glu Val Arg Asn Ser Thr Gly Leu Tyr His
 1               5                  10                  15

Val Thr Asn Asp Cys Pro Asn Ser Ser Ile Val Tyr Glu Thr Ala Asp
            20                  25                  30

Ala Ile Leu His Ala Pro Gly Cys Val Pro Cys Val Arg Glu Asp Asn
        35                  40                  45

Val Ser Arg Cys Trp Val Ala Met Thr Pro Thr Val Ala Thr Arg Asp
    50                  55                  60

Gly Lys Leu Pro Ala Thr Glu Leu Arg Arg His Ile Asp Leu Leu Val
65                  70                  75                  80
```

-continued

```
Gly Ser Ala Thr Leu Cys Ser Ala Leu Tyr Val Gly Asp Leu Cys Gly
                85                  90                  95

Ser Val Phe Leu Val Gly Gln Leu Phe Thr Phe Ser Pro Arg Arg His
            100                 105                 110

Trp Thr Thr Gln Asp Cys Asn Cys Ser Ile Tyr Pro Gly His Ile Thr
        115                 120                 125

Gly His Arg Met Ala Trp Asp Met Met Met Asn Trp Ser Pro Thr Thr
    130                 135                 140

Ala Leu Val Val Ala Gln Leu Val Arg Ile Arg Arg Pro Ala Ala Lys
145                 150                 155                 160

Leu Asn
```

(2) INFORMATION FOR SEQ ID NO: 7:

(i) SEQUENCE CHARACTERISTICS:
        (A) LENGTH: 489 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Hepatitis virus (ix) FEATURE:
        (A) NAME/KEY: CDS
        (B) LOCATION: 1.483

(xi) SEQUENCE DESCRIPTION: SEQ ID NO: 7:

```
ATG AGA GGA TCC GCT TAC GAA GTG CGC AAC TCC ACG GGG CTT TAC CAT       48
Met Arg Gly Ser Ala Tyr Glu Val Arg Asn Ser Thr Gly Leu Tyr His
  1               5                  10                  15

GTC ACC AAC GAT TGC CCC AAC TCG AGT ATT GTG TAC GAG ACA GCT GAT       96
Val Thr Asn Asp Cys Pro Asn Ser Ser Ile Val Tyr Glu Thr Ala Asp
             20                  25                  30

GCC ATC CTA CAC GCT CCG GGG TGC GTC CCT TGC GTT CGT GAG GAT AAC      144
Ala Ile Leu His Ala Pro Gly Cys Val Pro Cys Val Arg Glu Asp Asn
         35                  40                  45

GTC TCG AGG TGT TGG GTG GCG ATG ACC CCC ACG GTG GCC ACT AGG GAT      192
Val Ser Arg Cys Trp Val Ala Met Thr Pro Thr Val Ala Thr Arg Asp
 50                  55                  60

GGC AAA CTC CCC GCA ACG GAG CTT CGA CGT CAC ATC GAT CTG CTT GTC      240
Gly Lys Leu Pro Ala Thr Glu Leu Arg Arg His Ile Asp Leu Leu Val
 65                  70                  75                  80

GGG AGC GCC ACC CTC TGC TCG GCC CTT TAC GTG GGG GAC TTG TGC GGG      288
Gly Ser Ala Thr Leu Cys Ser Ala Leu Tyr Val Gly Asp Leu Cys Gly
                 85                  90                  95

TCT GTC TTT CTT GTC GGT CAG CTG TTT ACC TTC TCT CCC AGG CGC CAC      336
Ser Val Phe Leu Val Gly Gln Leu Phe Thr Phe Ser Pro Arg Arg His
            100                 105                 110

TGG ACG ACG CAA GAT TGC AAC TGT TCT ATC TAT CCC GGC CAT ATA ACG      384
Trp Thr Thr Gln Asp Cys Asn Cys Ser Ile Tyr Pro Gly His Ile Thr
        115                 120                 125

GGT CAC CGC ATG GCA TGG GAT ATG ATG ATG AAC TGG TCC CCT ACG ACG      432
Gly His Arg Met Ala Trp Asp Met Met Met Asn Trp Ser Pro Thr Thr
    130                 135                 140

GCA TTG GTA GTA GCT CAG CTG GTC CGG ATC CGT CGA CCT GCA GCC AAG      480
Ala Leu Val Val Ala Gln Leu Val Arg Ile Arg Arg Pro Ala Ala Lys
145                 150                 155                 160

CTT AAT TAG                                                          489
Leu Asn
```

(2) INFORMATION FOR SEQ ID NO: 8:

(i) SEQUENCE CHARACTERISTICS:
        (A) LENGTH: 300 base pairs
        (B) TYPE: nucleic acid
        (C) STRANDEDNESS: single
        (D) TOPOLOGY: linear (xi) SEQUENCE DESCRIPTION: SEQ ID NO: 8:

```
CC CTC ATG ACC GGC TAT ACC GGC GAC TTC GAC TCG GTG ATA GAC TGC        47
   Leu Met Thr Gly Tyr Thr Gly Asp Phe Asp Ser Val Ile Asp Cys
             5                  10                  15

AAC ACG TGT GTC ACT CAG ACA GTC GAT TTC AGC CTT GAC CCT ACC TTC       95
Asn Thr Cys Val Thr Gln Thr Val Asp Phe Ser Leu Asp Pro Thr Phe
                20                  25                  30

ACC ATT GAG ACG ACC ACA CTT CCC CAG GAT GCT GTC TCC CGC ACT CAA      143
Thr Ile Glu Thr Thr Thr Leu Pro Gln Asp Ala Val Ser Arg Thr Gln
                35                  40                  45

CGA CGG GGC AGG ACT GGC AGG GGG AAG CCG GGC ATC TAC AGA TTT GTC      191
Arg Arg Gly Arg Thr Gly Arg Gly Lys Pro Gly Ile Tyr Arg Phe Val
        50                  55                  60

GCA CCG GGG GAA CGC CCC TCC GGC ATG TTC GAC TCG TCC GTC CTC TGT      239
Ala Pro Gly Glu Arg Pro Ser Gly Met Phe Asp Ser Ser Val Leu Cys
        65                  70                  75

GAG TGC TAT GAC GCA GGT TGT GCT TGG TAT GAG CTC ACG CCC GCC GAG      287
Glu Cys Tyr Asp Ala Gly Cys Ala Trp Tyr Glu Leu Thr Pro Ala Glu
 80                  85                  90                  95

TGAATTCAAG CTT                                                       300
```

(2) INFORMATION FOR SEQ ID NO: 9:

(i) SEQUENCE CHARACTERISTICS:
        (A) LENGTH: 219 base pairs
        (B) TYPE: nucleic acid
        (C) STRANDEDNESS: single
        (D) TOPOLOGY: linear (xi) SEQUENCE DESCRIPTION: SEQ ID NO: 9:

```
ATC CCC TTT GTG TCC TGC CAG CGC GGG TAT AGG GGG GCC TGG CGA GGG       48
Ile Pro Phe Val Ser Cys Gln Arg Gly Tyr Arg Gly Ala Trp Arg Gly
             5                  10                  15

GAC GGC ATC ATG CAC ACT CGC TGC CAC TGT GGA GCT GAG ATC ACC GGA       96
Asp Gly Ile Met His Thr Arg Cys His Cys Gly Ala Glu Ile Thr Gly
                20                  25                  30

CAT GTC AAG AAC GGG ACG ATG AGG ATC GTC GGT CCT AAG ACC TGC AGG      144
His Val Lys Asn Gly Thr Met Arg Ile Val Gly Pro Lys Thr Cys Arg
                35                  40                  45

AAC ATG TGG AGT GGG ACC TTC CCC ATT AAT GCC TAC ACC ACG GGC CCC      192
Asn Met Trp Ser Gly Thr Phe Pro Ile Asn Ala Tyr Thr Thr Gly Pro
        50                  55                  60

TGT ACC CCC CTT CCT GCG CCG AAC TAT                                  219
Cys Thr Pro Leu Pro Ala Pro Asn Tyr
 65                  70
```

(2) INFORMATION FOR SEQ ID NO: 10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 10:

```
GGGAGTGAAG CAATATACCG GACC                                              24

(2) INFORMATION FOR SEQ ID NO: 11:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 11:

CCGATTTTGA CCAGGGCTGG GGCCCTATCA GTTAT                                  35

(2) INFORMATION FOR SEQ ID NO: 12:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO: 12:

GAGGGATCCA TCATGAGCAC AAATCCTAAA CC                                     32

(2) INFORMATION FOR SEQ ID NO: 13:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 13:

GAGAAGCTTA GGAAGCGGGG ATGGTTCAAG C                                      31

(2) INFORMATION FOR SEQ ID NO: 14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 14:

GAGGGATCCG CTTACGGAGT GGGCAAC                                           27

(2) INFORMATION FOR SEQ ID NO: 15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 15:

GAGGGATCCG GACCAGCTTG AGCTACTAC                                         29

(2) INFORMATION FOR SEQ ID NO: 16:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 16:

CGGAAGCTTA CCTACGCCGG GGGTCTGTGG G                                      31
```

(2) INFORMATION FOR SEQ ID NO: 17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 17:

CTGCCTGGGA TCCCCTTTGT GTCC        24

(2) INFORMATION FOR SEQ ID NO: 18:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 18:

GGAAAGCTTA AGCGGATAGC TGGCTAGCCG AGGAG        35

(2) INFORMATION FOR SEQ ID NO: 19:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 19:

GAGGGATCCA GGGGATCACC CCCCTCTGTG GCC        33

(2) INFORMATION FOR SEQ ID NO: 20:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO: 20:

GAGAAGCTTG AATTCTATGT GACTTTCTTC TGCCTTTGGC AAG        43

(2) INFORMATION FOR SEQ ID NO: 21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 21:

AAGGGATCCG GCCGGGAGAT ACTGCTCGGG        30

(2) INFORMATION FOR SEQ ID NO: 22:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO: 22:

GGCAAGCTTG AATTCAGATG TTAGGATCGA TCCCATGAG        39

(2) INFORMATION FOR SEQ ID NO: 23:

```
        (i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO: 23:

GGAGGATCCG CTCATGGGAT CGATCCTAAC                                        30

(2) INFORMATION FOR SEQ ID NO: 24:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (xi) SEQUENCE DESCRIPTION: SEQ ID NO: 24:

GGAAGCTTGA ATTCACTCGG CGGGCGTGAG CTCATACCAA G                           41

(2) INFORMATION FOR SEQ ID NO: 25:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (xi) SEQUENCE DESCRIPTION: SEQ ID NO: 25:

GGAGGATCCC CCACCCTCCA TGGGCCAACA CCCC                                   34

(2) INFORMATION FOR SEQ ID NO: 26:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (xi) SEQUENCE DESCRIPTION: SEQ ID NO: 26:

GGGAAGCTTG AATTCAAAGA GCTCCCGCCA CGCCCGC                                37
```